(12) United States Patent
Kayahara

(10) Patent No.: US 7,952,715 B2
(45) Date of Patent: May 31, 2011

(54) PRINTING DEVICE, METHOD OF CONTROLLING PRINTING DEVICE, AND RECORDING MEDIUM

(75) Inventor: Naoki Kayahara, Chino (JP)

(73) Assignee: Seiko Epson Corporation, Tokyo (JP)

( * ) Notice: Subject to any disclaimer, the term of this patent is extended or adjusted under 35 U.S.C. 154(b) by 516 days.

(21) Appl. No.: 12/050,781

(22) Filed: Mar. 18, 2008

(65) Prior Publication Data

US 2008/0231858 A1    Sep. 25, 2008

(30) Foreign Application Priority Data

Mar. 20, 2007  (JP) ................................. 2007-072003

(51) Int. Cl.
*G01N 21/55*  (2006.01)

(52) U.S. Cl. ....................................................... 356/445

(58) Field of Classification Search .................. 356/445, 356/237.1, 238.1; 399/74; 355/40, 41
See application file for complete search history.

(56) References Cited

U.S. PATENT DOCUMENTS

| | | | |
|---|---|---|---|
| 5,925,889 A * | 7/1999 | Guillory et al. | .......... 250/559.16 |
| 6,373,575 B1 | 4/2002 | Takayama et al. | |
| 6,894,262 B2 | 5/2005 | Gao et al. | |
| 2003/0132366 A1 | 7/2003 | Gao et al. | |
| 2006/0256341 A1 | 11/2006 | Kuwada | |
| 2007/0058204 A1 * | 3/2007 | Kakutani | ..................... 358/3.13 |

FOREIGN PATENT DOCUMENTS

| | | |
|---|---|---|
| JP | 09-015151 | 1/1997 |
| JP | 2000088769 A | 3/2000 |
| JP | 2000206054 A | 7/2000 |
| JP | 2005515412 A | 5/2005 |
| JP | 2006284550 A | 8/2009 |

* cited by examiner

*Primary Examiner* — Tarifur Chowdhury
*Assistant Examiner* — Michael LaPage
(74) *Attorney, Agent, or Firm* — DLA Piper LLP (US)

(57) ABSTRACT

A printing device calculates a status value of a surface of a print medium to determine the appropriateness of the print medium for printing. Light fluxes are inputted to the surface of the print medium at an incidence angle. An image pickup unit picks up reflection light fluxes and a measurement-target surface status value calculating unit calculates a status value relating to the appropriateness of the print medium for printing based on the picked up luminance information.

12 Claims, 7 Drawing Sheets

PRINTING DEVICE, METHOD OF CONTROLLING PRINTING DEVICE, AND RECORDING MEDIUM

BACKGROUND

1. Technical Field

The present invention relates to a printing device, a method of controlling a printing device, and a recording medium capable of calculating a status value of a measurement-target surface which represents a status of the measurement-target surface of a print medium and a printing device, a method of controlling a printing device, and a recording medium capable of sorting a print medium based on the status value of the measurement-target surface.

2. Related Art

There are various types of print sheets, and, for example, there are a sheet (gloss sheet) having a gloss effect close to a print-dedicated sheet and the like.

Among gloss sheets, there is a plurality of types of the gloss sheets developed for a laser printer, an ink jet printer, and the like, and some types of the gloss sheets do not particularly require non-uniformity of paper quality (a surface status and the like) depending on the use thereof (for example, the gloss sheets for a laser printer). When a printing process is performed on such gloss sheets by using an inkjet printer, there is a case where non-uniformity of density occurs. In addition, there is a case where the degree of the non-uniformity of density occurs differently for each sheet.

As technology for measuring a light diffusion property of a measurement-target surface of an object to be measured, for example, there is a diffusion property measuring device disclosed in JP-A-9-15151.

In the diffusion property measuring device disclosed in JP-A-9-15151, the measurement-target surface of the object to be measured is projected with parallel light fluxes which have been formed by a projection lens using light fluxes emitted from a light source, light fluxes diffused by being transmitted through or reflected from the projected measurement-target surface are collected by using a light collecting lens having a font focus in an approximate center of the spot, and the diffused light fluxes are detected by a photoelectric conversion unit constituted by a plurality of photoelectric elements disposed in light pathways of light fluxes output from the light collecting lens for measuring the diffusion property of the measuring-target surface.

However, the object of the technology disclosed in JP-A-9-15151 is to measure the diffusion direction of light fluxes diffused on the surface of the object to be measured and diffusion strength in the direction in a short time, and information that can be used for determining whether the surface status of the object to be measured is appropriate for printing or the like is not generated.

SUMMARY

An advantage of some aspects of the invention is that it provides a printing device, a method of controlling a printing device, and a recording medium capable of calculating a status value of a measurement-target surface which represents a status relating to an appropriateness or inappropriateness of the measurement-target surface for printing and a printing device, a method of controlling a printing device, and a recording medium capable of sorting a print medium based on the status value of the measurement-target surface.

According to a first aspect of the invention, there is provided a printing device including: a light input unit that inputs light fluxes emitted from a light source on a measurement-target surface of a print medium on which an image is printed at a predetermined incidence angle; an image pickup unit that picks up an image of the measurement-target surface by collecting reflection light fluxes for the light fluxes input by the light input unit which are reflected from the measurement-target surface of the print medium within a predetermined range of reflection angles, receiving the collected light fluxes using a plurality of light receiving elements, and performing a photoelectric conversion process for the light fluxes received by the plurality of light receiving elements; and a measurement-target surface status value calculating unit that calculates a status value of the measurement-target surface representing a status relating to appropriateness or inappropriateness of the measurement-target surface of the print medium for printing based on image data having luminance information of the image picked up by the image pickup unit.

According to the printing device, there is an advantage that whether the status of the measurement-target surface is appropriate for printing can be predicted or determined on the basis of the status value of the measurement-target surface which representing a status regarding to appropriateness or inappropriateness of the measurement-target surface of the print medium.

In addition, since there are printing devices of various printing types including a laser printer, an ink jet printer, and the like, the prediction (determination) on whether the status of the measurement-target surface is appropriate for printing can be performed in accordance with the printing types. For example, prediction (determination) that a print medium is appropriate for a laser printer (for example, a gloss sheet or the like) and not appropriate for an ink jet printer can be made.

Here, a print sheet, a CD or a DVD having a measurement-target surface, or the like corresponds to the print medium. In addition, a material forming the measurement-target surface is different depending on the printing types such as a print medium for a laser printer or a print medium for an ink jet printer. In addition, there are a plain sheet, a gloss sheet, and the like depending on its use. The above-described description also applies to a recording medium and a method of controlling a printing device according to embodiments of the invention to be described below.

In addition, for example, a photo diode or the like corresponds to the light receiving. The above-described description also applies to a recording medium and a method of controlling a printing device according to embodiments of the invention to be described below.

In addition, for example, a device using technology such as CCD (Charge-Coupled Device) technology or CMOS technology corresponds to the photoelectric conversion element. The above-described description also applies to a recording medium and a method of controlling a printing device according to embodiments of the invention to be described below.

Regarding the above-described status relating to appropriateness or inappropriateness for printing, for example, as an appropriate status, there is a status (for example, a status that non-uniformity of gloss is small) that the measurement-target surface is smooth. In particular, a status that a printing result of excellent quality without occurring non-uniformity of density for most of the time is acquired corresponds to the appropriate status. On the other hand, as the inappropriate status, there is a status (for example, non-uniformity of gloss is large) that the measurement-target surface is rough. In particular, a status that a printing result of a bad quality due to occurrence of noticeable non-uniformity of density is acquired or the like corresponds to the inappropriate status. The above-described description also applies to a recording medium and a method of controlling a printing device according to embodiments of the invention to be described below.

According to a second aspect of the invention, in the printing device according to the first aspect, the measurement-target surface status value calculating unit calculates the status value of the measurement-target surface based on an RMS (Root Mean Square) granularity that is a standard deviation of distribution of the luminance information included in the image data of the measurement-target surface.

According to the printing device, the status value of the measurement-target surface is calculated based on the RMS granularity that can be used for determining the degree of granularity of the image, and accordingly, it can be determined whether the measurement-target surface of the medium is rough or smooth based on the status value, and thereby an advantage that a print medium appropriate for printing and a print medium inappropriate for printing can be predicted (determined) more appropriately based on the status value is acquired.

According to a third aspect of the invention, the printing device according to the first aspect further includes: a frequency converting unit that converts the luminance information included in the image data of the measurement-target surface into information on spatial frequencies; and a correction unit that corrects the information on spatial frequencies converted by the frequency converting unit using a parameter of human visual spatial frequency characteristics (VTF: Visual Transfer Function). The measurement-target surface status value calculating unit calculates the status value of the measurement-target surface based on the total amount of power of the spatial frequencies which have been corrected by the correction unit.

According to the printing device, luminance information included in the image data of the measurement-target surface can be converted into information on the spatial frequencies by the frequency converting unit and the information on the spatial frequencies converted by the frequency converting unit can be corrected by the correction unit using a parameter of human visual spatial frequency characteristics (VTF: Visual Transfer Function).

In addition, the status value of the measurement-target surface can be calculated based on the total amount of power of the spatial frequencies, which have been corrected by the correction unit, by the measurement-target surface status value calculating unit.

Since the status value of the measurement-target surface is calculated based on the information (the total amount of power) on the spatial frequencies adjusted for human visual characteristics, an advantage that a print medium appropriate for printing and a print medium inappropriate for printing can be predicted (determined) more precisely based on the status value is acquired.

According to a fourth aspect of the invention, in the printing device according to the first aspect, the light input unit and the image pickup unit are disposed such that an incidence angle of a flux positioned in the center or an approximate center of the input light fluxes and a reflection angle of a light flux positioned in the center or an approximate center of the reflection light fluxes received by the plurality of light receiving elements are identical to each other.

According to the printing device, reflection light fluxes (reflection light fluxes reflected regularly) appropriate to representing the status relating to appropriateness or inappropriateness of the measuring-target surface for printing can be received by the image pickup unit, and accordingly, an advantage that the status value of the measuring-target surface representing a more precise status relating to appropriateness or inappropriateness of the measuring-target surface for printing can be calculated is acquired.

According to a fifth aspect of the invention, there is provided a recording medium having embodied thereon a program that allows a computer to perform calculating a status value of a measurement-target surface representing a status relating to appropriateness or inappropriateness of the measurement-target surface of a print medium for printing based on image data including luminance information of an image acquired by an image pickup unit that picks up the image of the measurement-target surface by collecting reflection light fluxes, which are reflected from the measurement-target surface of the print medium within a predetermined range of reflection angles, for light fluxes incident at a predetermined incidence angle to the measurement-target surface of the print medium, receiving the collected light fluxes using a plurality of light receiving elements, and performing a photoelectric conversion process for the light fluxes received by the plurality of light receiving elements.

According to the recording medium, when the program is read out by a computer and the computer performs a process in accordance with the program, the same processes and advantages as those of the printing device according to the first aspect are acquired.

In addition, by rewiring a part of the program, version up of the program due to modification or improvement of a function can be performed in an easy manner.

In addition, in this aspect, a configuration in which functions achieved by each unit of the printing device according to the first to fourth aspects are implemented as a computer-readable program may be used.

According to a sixth aspect of the invention, there is provided a method of controlling a printing device. The method includes: inputting light fluxes emitted from a light source to a measurement-target surface of a print medium at a predetermined incidence angle; picking up an image of the measurement-target surface by collecting reflection light fluxes, which are reflected from the measurement-target surface of the print medium within a predetermined range of reflection angles, for the light fluxes input by the inputting of light fluxes, receiving the collected light fluxes using a plurality of light receiving elements, and performing a photoelectric conversion process for the light fluxes received by the plurality of light receiving elements; and calculating a status value of the measurement-target surface representing a status relating to appropriateness or inappropriateness of the measurement-target surface of the print medium for printing based on image data having luminance information of the image picked up by the picking up of an image.

According to the method, the same processes and advantages as those of the printing device according to the first aspect can be acquired.

In addition, in this aspect, a configuration in which each unit of the printing device according to the first to fourth aspects is replaced with a corresponding process may be used.

According to a seventh aspect of the invention, in the printing device according to the first aspect, a sorting unit that sorts print media into types according to the status values of the measurement-target surfaces based on the status values of the measurement-target surfaces calculated by the measurement-target surface status value calculating unit is further included.

According to the printing device, print media can be sorted into types according to the status values of the measurement-target surfaces based on the status values of the measurement-target surfaces calculated by the measurement-target surface status value calculating unit according to the first aspect, by using the sorting unit.

Accordingly, for example, a predetermined range of the status values of the measuring-target surfaces is divided into a plurality of ranges, and the print media can be sorted in accordance with the divided ranges. Accordingly, an advantage that the print media can be sorted in accordance with printing qualities of the print media in an easy manner is acquired.

According to an eighth aspect of the invention, in the printing device according to the seventh aspect, a prediction unit that predicts whether a defective quality of printing occurs in a case where a print medium corresponding to the status value of the measurement-target surface is used for printing based on the status value of the measurement-target surface which is calculated by the measurement-target surface status value calculating unit is further included, and the sorting unit sorts the print medium based on the result of prediction of the prediction unit.

According to the printing device, it is possible to sort a print medium predicted (determined) to generate a defective quality of printing and a print medium predicted (determined) not to generate a defective quality of printing.

According to the printing device, a print medium determined to generate a defective quality of printing can be excluded before a printing process, and accordingly an advantage that prints with high quality can be stably acquired is acquired.

According to a ninth aspect of the invention, in the recording medium according to the fifth aspect, the program further allows a computer to perform sorting print media into types according to the status values of the measurement-target surfaces based on the status values of the measurement-target surfaces calculated by the calculating of a status value.

According to the recording to the recording medium, when the program is read out by a computer and the computer performs a process in accordance with the program, the same processes and advantages as those of the printing device according to the seventh aspect are acquired.

In addition, by rewiring a part of the program, version up of the program due to modification or improvement of a function can be performed in an easy manner.

In addition, in this aspect, a configuration in which functions achieved by each unit of the printing device according to any one of the second to fourth aspects are implemented as a computer-readable program may be used. In addition, in this aspect, a configuration in which functions achieved by each unit of the printing device according to the eighth aspect are implemented as a computer-readable program may be used.

According to a tenth aspect of the invention, in the method according to the sixth aspect, sorting print media into types according to the status values of the measurement-target surfaces based on the status values of the measurement-target surfaces calculated by the calculating of a status value is further included.

According to the method, the same processes and advantages as those of the printing device according to the seventh aspect can be acquired.

In addition, in this aspect, a configuration in which each unit of the printing device according to any one of the first to fourth aspects is replaced with a corresponding process may be used. In addition, in this aspect, a configuration in which each unit of the printing device according to the eighth aspect is replaced with a corresponding process may be used.

BRIEF DESCRIPTION OF THE DRAWINGS

The invention will be described with reference to the accompanying drawings, wherein like numbers reference like elements.

DESCRIPTION OF EXEMPLARY EMBODIMENTS

Hereinafter, embodiments of the present invention will be described with reference to the accompanying drawings. FIGS. 1 to 9 are diagrams showing a printing device, a recording medium, and a method of controlling a printing device according to embodiments of the invention.

Figure 1:
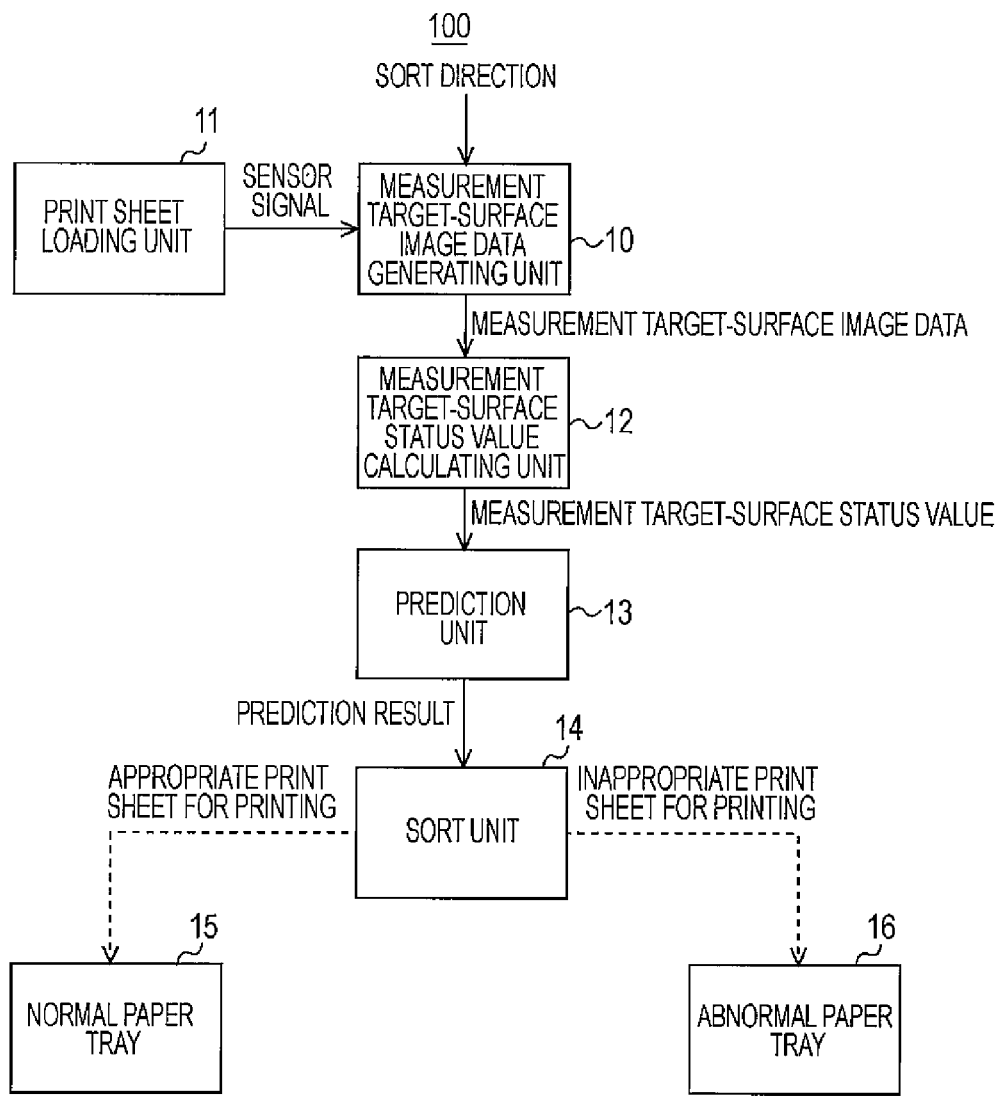
FIG. 1 is a block diagram showing the configuration of a sorting device 100 according to an embodiment of the invention.

First, the configuration of a printing device according to an embodiment of the invention will be described with reference to FIG. 1. FIG. 1 is a block diagram showing the configuration of a sorting device 100 according to an embodiment of the invention.

The printing device 100, as shown in FIG. 1, is configured to include a measurement-target surface image data generating unit 10 that generates image data of a measurement-target surface, a print sheet loading unit 11 that loads a print sheet to be sorted, a measurement-target surface status value calculating unit 12 that calculates a status value of the measurement-target surface representing the status of a measurement-target surface, a prediction unit 13 that predicts a status relating to whether the measurement-target surface is appropriate for printing, a sorting unit 14 that sorts print sheets based on the result of prediction for a measurement-target surface, a normal paper tray 15, and an abnormal paper tray 16.

The measurement-target surface image data generating unit 10 has a function for picking up an optical image formed by regular reflection light of the measurement-target surface of the print sheet loaded by the print sheet loading unit 11 and outputting image data of the picked-up image to the measurement-target surface status value calculating unit 12.

The print sheet loading unit 11 has a tray that loads a plurality of print sheets and a sensor that detects whether a print sheet is loaded. The print sheet loading unit 11 has a function for outputting a signal from the sensor to the measurement-target surface image data generating unit 10.

The measurement-target surface status value calculating unit 12 has a function for calculating a status value of the measurement-target surface representing a status relating to whether a measurement-target surface is appropriate for printing based on the image data of a measurement-target surface of a print sheet input from the measurement-target surface image data generating unit 10.

In this embodiment, the measurement-target surface status value calculating unit 12 can calculate an RMS granularity of image data of a measurement-target surface of a print sheet and a total amount of power of spatial frequencies of the image data as a status value of the measurement-target surface.

The prediction unit 13 compares the status value of the measurement-target surface (the RMS granularity or the total amount of power) calculated by the measurement-target surface status value calculating unit 12 with a threshold value prepared in advance and predicts whether the status of the measurement-target surface is appropriate for printing. The threshold value is configured to be stored in one between a ROM 64 and a storage device 70, which will be described later, in advance.

The sorting unit 14 has a transport mechanism not shown in the figure. Based on the prediction result of the prediction unit 13, the sorting unit 14 drives the transport mechanism so as to transport the target print sheet to the normal paper tray 15 in a case where the target print sheet is predicted to be appropriate for printing, and drives the transport mechanism so as to transport the target print sheet to the abnormal paper tray 16 in a case where the target print sheet is predicted to be inappropriate for printing.

The normal paper tray 15 is a tray dedicated for storing the print sheet that has been predicted to be appropriate for printing by the prediction unit 13.

The abnormal paper tray 16 is a tray dedicated for storing the print sheet that has been predicted to be inappropriate for printing by the prediction unit 13.

Hereinafter, a detailed configuration of the measurement-target surface image data generating unit 10 will be described with reference to FIG. 2.

Figure 2:
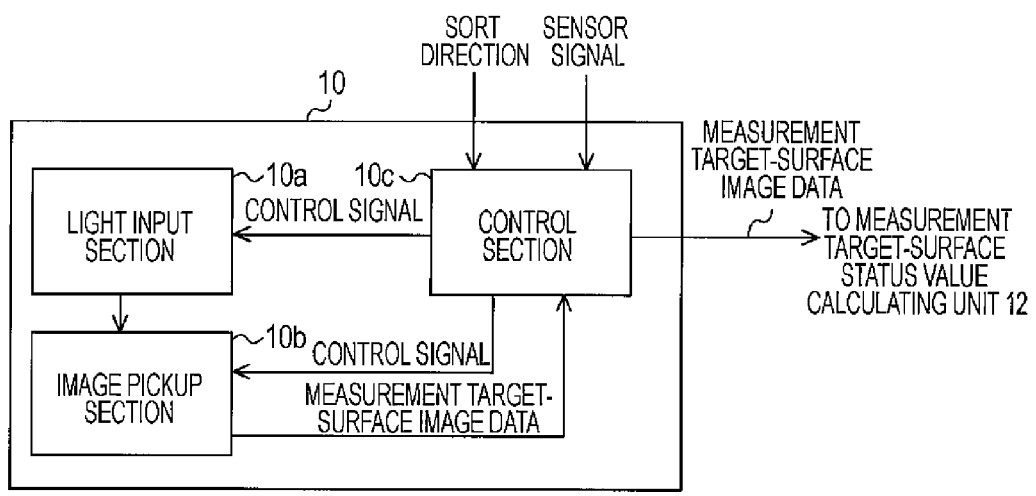
FIG. 2 is a block diagram showing a detailed configuration of a measurement-target surface image data generating unit 10 according to an embodiment of the invention.

Here, FIG. 2 is a block diagram showing a detailed configuration of the measurement-target surface image data generating unit 10.

The measurement-target surface image data generating unit 10, as shown in FIG. 2, is configured to include a light input section 10a, an image pickup section 10b, and a control section 10c.

The light input section 10a has a light source and a light collecting lens. The light input section 10a has functions for collecting light fluxes from the light source using the light collecting lens and inputting (projecting) the light fluxes to the measurement-target surface of a print sheet at a predetermined incidence angle by adjusting a projection angle (approximately parallelized) in accordance with a control signal from the control section 10c. Accordingly, the light collecting lens has a function for adjusting the projection angle in addition to the function of collecting light.

The image pickup section 10b is configured to include a light collecting lens that collects reflection light fluxes reflected from the measurement-target surface within a predetermined range of reflection angles for light fluxes incident to the measurement-target surface of the print sheet from the light input section 10a, a plurality of light receiving elements (photodiodes or the like) that receives the reflection light fluxes collected by the light collecting lens, and a photoelectric conversion element (CCDs or the like) that performs a photoelectric conversion process for the light fluxes received by the plurality of the light receiving elements so as to generate pixel signals. The light receiving elements and the photoelectric conversion element constitute a sensor cell (pixel), and a plurality of the sensor cells is configured to be arranged in a matrix shape. Accordingly, the plurality of the sensor cells outputs pixel signals based on the intensity of light received by the sensor cells.

In addition, the image pickup section 10b has an exposure time control device (ALC) and an A/D converter for converting analog pixel signal data into digital pixel data which are not shown in the figure and the like.

The image pickup section 10b receives light fluxes reflected from the measurement-target surface for a predetermined exposure time in accordance with a control signal from the control section 10c and generates digital image data of the image of the measurement-target surface based on pixel signals that are photoelectric-converted in a plurality of sensor cells.

The image data of the measurement-target surface is not necessarily the image data of the whole measurement-target surface of a print sheet and may be image data of a partial measurement-target surface. In order to increase the prediction precision, it is preferable to generate image data of a large area as possibly as can be. However, when the area is too large, the calculation processing time required for the measurement-target surface status value calculating unit 12 becomes long. Accordingly, it is preferable to generate image data of an area for which balance of the prediction precision and the calculation processing time is excellent.

To the control section 10c, a sorting direction from a user is input through an input device 74 described later. The control section 10c outputs a control signal to the light input section 10a and the image pickup section 10b when a print sheet is detected based on a sensor signal transmitted from the print sheet loading unit 11. In addition, the control section 10c acquires the image data generated by the image pickup section 10b and outputs the acquired image data to the measurement-target surface status value calculating unit 12.

Next, dispositional relationship between the light input section 10a and the image pickup section 10b will be described with reference to FIG. 3.

Figure 3:
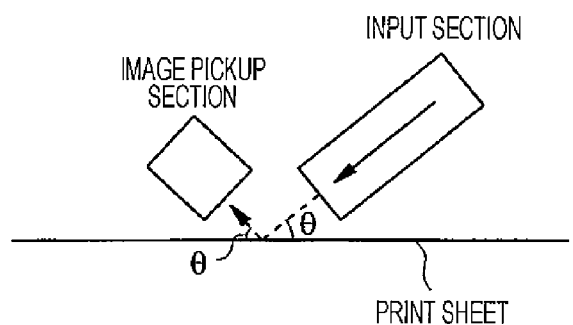
FIG. 3 is a diagram showing an example of a dispositional configuration of a light input section 10a and an image pickup section 10b according to an embodiment of the invention.

Here, FIG. 3 is a diagram showing an example of a dispositional configuration of the light input section 10a and the image pickup section 10b.

First, according to this embodiment, in order to acquire the status of a measurement-target surface of an unused print sheet, image data of the measurement-target surface is generated. Thus, it is preferable that only regular reflection light that is regularly reflected (reflected at a same angle as the incidence angle) from the measurement-target surface is incident to the image pickup section 10b.

For example, when the measurement-target surface is in a smooth status (for example, a status of a glass surface), the amount of light that is regularly reflected from the measurement-target surface among light fluxes incident from the light input section 10a is large. On the other hand, when the measurement-target surface is in a rough status (for example, a status of a surface having many concaves and convexes), the amount of light that is irregularly reflected from the measurement-target surface among light fluxes incident from the light input section 10a is large. In other words, an image created by regular reflection light only, for example, becomes an image in which over-exposed pixels are uniformly distributed (luminance change is small). On the other hand, when the amount of irregular reflection light is large, the amount of regular reflection light is small, and, the image, for example, becomes an image in which over-exposed pixels are non-uniformly distributed (luminance change is large).

In this embodiment, in consideration of uniformity of over-exposed pixels (luminance change (distribution)), a surface data of the measurement-target surface which can be used for determining whether the measurement-target surface is appropriate for printing is calculated based on the distribution of the over-exposed pixels.

Thus, according to this embodiment, as shown in FIG. 3, the light input section 10a is disposed such that a light flux in the center or approximate center of the incident light fluxes has an incidence angle of θ (for example, 45°) with respect to the measurement-target surface, and the image pickup section 10b is disposed such that a light ray in the center of light fluxes regularly reflected at a reflection angle θ (the same angle as the incidence angle) with respect to the incident light fluxes passes though the center or approximate center of a light collecting lens included in the image pickup section 10b. In other words, the light input section 10a and the image pickup section 10b are disposed such that an angle θ formed by a projection direction of the light fluxes of the light input section 10a and the measurement-target surface and an angel θ formed by the direction for input of the regular reflection light fluxes of the image pickup section 10b and the measurement-target surface are identical to each other. Accordingly, most of the reflection light incident to the image pickup section 10b is regular reflection light.

Figure 4:
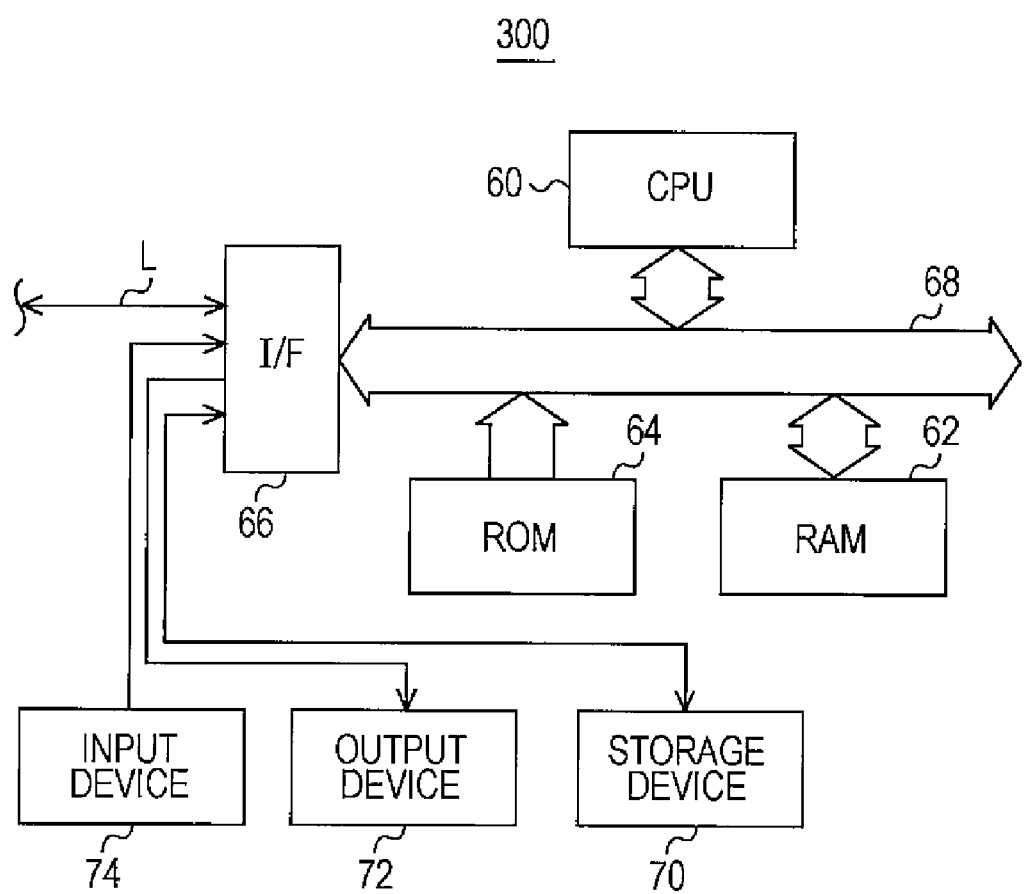
FIG. 4 is a block diagram showing a hardware configuration of a computer system 300 according to an embodiment of the invention.

In addition, in order to implement the above-described functions of the measurement-target surface image data generating unit 10, the measurement-target surface status value calculating unit 12, the prediction unit 13, the sorting unit 14, and the like in software and execute software for controlling hardware required for implementing the above-described functions, the printing device 100 includes a computer system 300. The computer system 300, as shown in FIG. 4, has a hardware configuration in which a CPU (Central Processing Unit) 60 that is a central calculation processing device responsible for various control processes and calculation processes, a RAM (Random Access Memory) 62 constituting a main storage device (Main Storage), and a ROM (Read Only Memory) 64 that is a storage device only for reading data are interconnected together with various internal and external buses 68 constituted by a PCI (Peripheral Component Interconnect) bus, an ISA (Industrial Standard Architecture) bus, or the like, and a storage device (Secondary Storage) 70 such as a HDD, an output device 72 such as a CRT or an LCD monitor, an input device 74 such as an operation panel, a mouse, or a keyboard, a sorting direction device (not shown), a network cable L for communication, and the like are connected to the buses 68 though an input/output interface (I/F) 66.

When the power is turned on, a system program such as a BIOS that is stored in the ROM 64 or the like loads various special purpose programs, which are stored in advance in the ROM 64, into the RAM 62 and the CPU 60 performs predetermined control and calculation processes by using various resources in accordance with commands described in the programs loaded in the RAM 62, and thereby the above-described functions are configured to be implemented in software.

Next, the flow of a sorting process in the above-described printing device 100 will be described with reference to FIG. 5.

Figure 5:
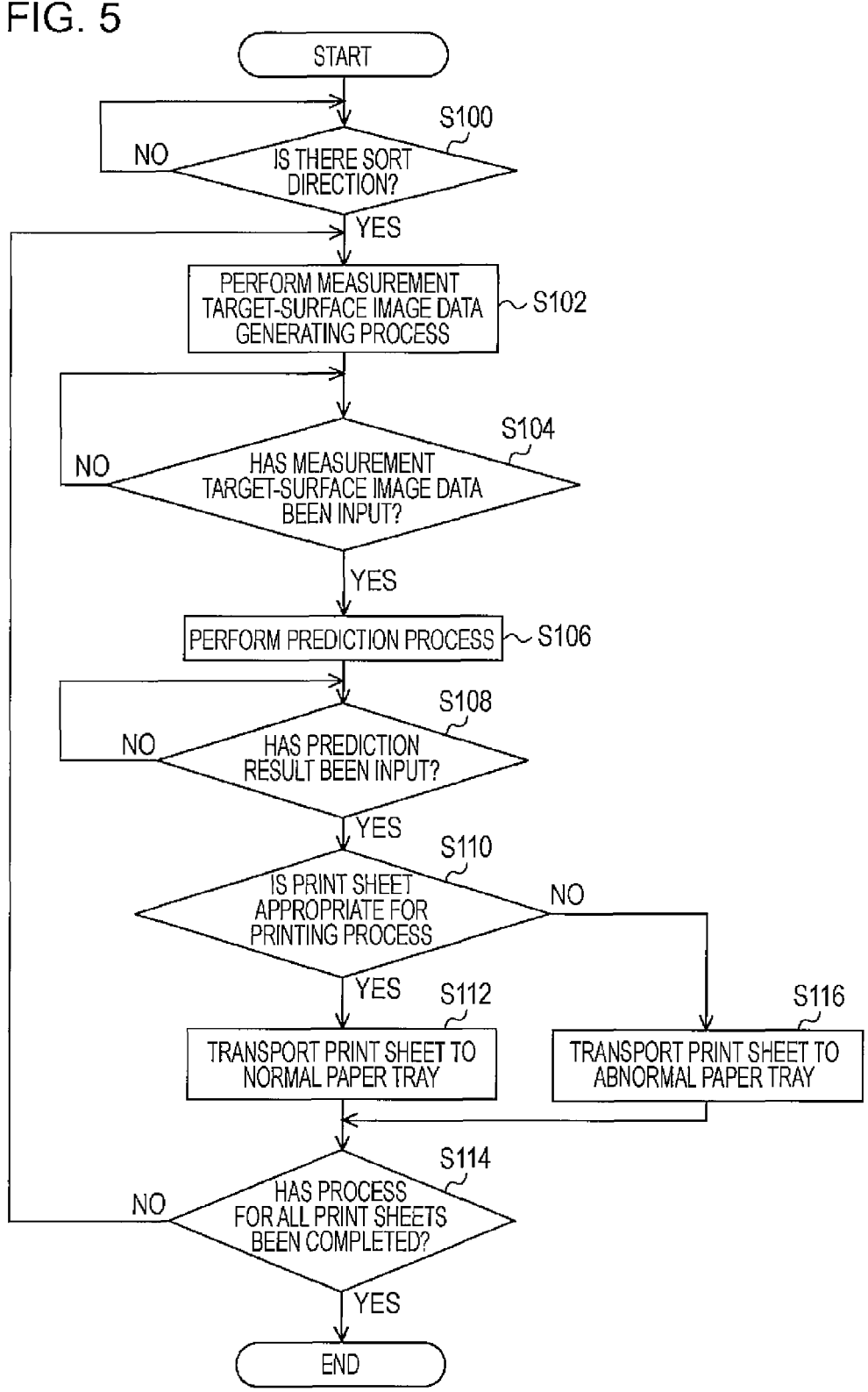
FIG. 5 is a flowchart showing a sorting process of the printing device 100.

Here, FIG. 5 is a flowchart showing the sorting process of the printing device 100.

The sorting process, as shown in FIG. 5, first, proceeds to Step S100, and the measurement-target surface image data generating unit 10 determines whether there is a sorting direction from a sorting direction terminal (not shown) or the like such as a PC. When it is determined that there is a sorting direction (Yes), the process proceeds to Step S102. On the other hand. When it is determined that there is not a sorting direction (No), the determination process is repeated until there is a sorting direction.

When the process proceeds to Step S102, the measurement-target surface image data generating unit 10 performs a process for generating measurement-target surface image data for a print sheet loaded by the print sheet loading unit 11, and the process proceeds to Step S104.

In Step S104, the measurement-target surface status value calculating unit 12 determines whether the measurement-target surface image data has been input from the measurement-target surface image data generating unit 10. When it is determined that the measurement-target surface image data has been input (Yes), the process proceeds to Step S106. On the other hand, when it is determined that the measurement-target surface image data has not been input (No), the determination process is repeated until the measurement-target surface image data is input.

When the process proceeds to Step S106, the measurement-target surface status value calculating unit 12 and the prediction unit 13 perform a prediction process based on the measurement-target surface image data input in Step S104, and the process proceeds to Step S108.

In Step S108, the sorting unit 14 determines whether the result of prediction has been input from the prediction unit 13. When it is determined that the result of the prediction has been input (Yes), the process proceeds to Step S110. On the other hand, when it is determined that the result of the prediction has not been input (No), the determination process is repeated until the result of the prediction is input.

When the process proceeds to Step S110, the sorting unit 14 determines whether the print sheet is appropriate for printing based on the result of the prediction input in Step S108. When the print sheet is determined to be appropriate for printing (Yes), the process proceeds to Step S112. On the other hand, when the print sheet is determined not to be appropriate for printing (No), the process proceeds to Step S116.

When the process proceeds to Step S112, the sorting unit 14 transports the print sheet to the normal paper tray 15, and the process proceeds to Step S114.

In Step S114, the measuring-target surface image data generating unit 10 determines whether the sorting process for all the print sheets has been completed based on the sensor signal from the print sheet loading unit 11. When it is determined that the sorting process has been completed (Yes), the process ends. On the other hand, when it is determined that the sorting process has not been completed (No), the process proceeds to Step S102.

Next, the flow of the process for generating the measuring-target surface image data performed by the measuring-target surface image data generating unit 10 in Step S102 will be described with reference to FIG. 6.

Figure 6:
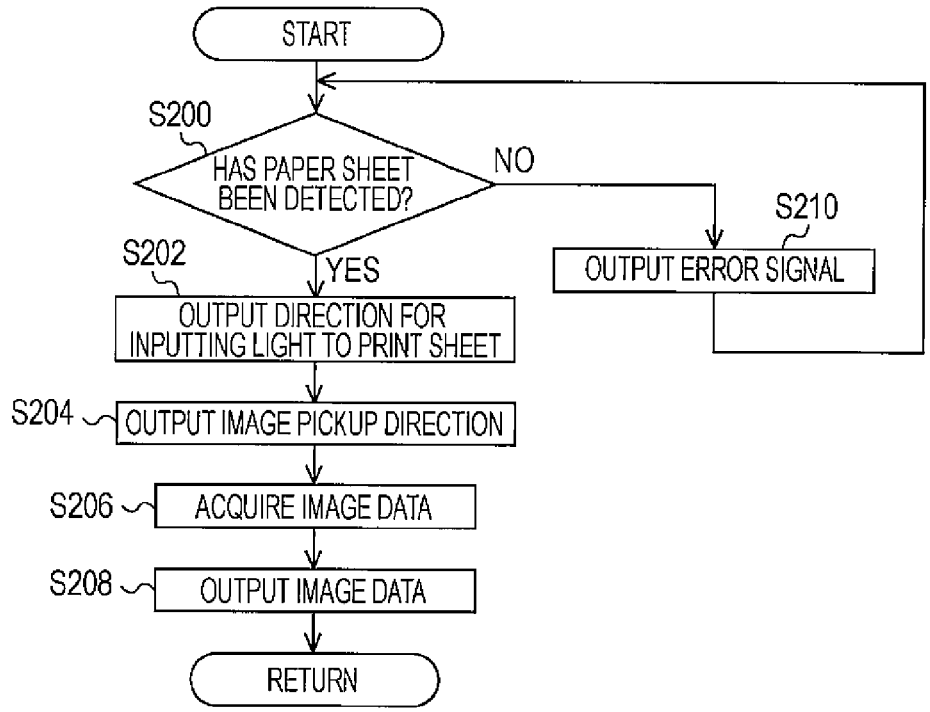
FIG. 6 is a flowchart showing a process for generating the measuring-target surface image data performed by the measuring-target surface image data generating unit 10.

Here, FIG. 6 is a flowchart showing the process for generating the measuring-target surface image data performed by the measuring-target surface image data generating unit 10.

When a sorting direction is input and the process for generating the measuring-target surface image data is started in Step S102, as shown in FIG. 6, first, the process proceeds to Step S200, and the control section 10c determines whether a print sheet is detected based on a sensor signal from the print sheet loading unit 11. When it is determined that the paper is detected (Yes), the process proceeds to Step S202. On the other hand, when it is determined that the paper is not detected (No), an error signal is output, and the process proceeds to Step S200.

When the process proceeds to Step S202, the control section 10c outputs a direction (control signal) for inputting light fluxes to the light input section 10a, and the process proceeds to Step S204.

In Step S204, the control section 10c outputs a direction (control signal) for picking up an image to the image pickup section 10b, and the process proceeds to Step S206.

In Step S206, the control section 10c acquires image data of an image acquired by an image pickup process performed by the image pickup section 10b, and the process proceeds to Step S208.

In Step S208, the control section 10c outputs the image data of the measuring-target surface which has been acquired in Step S206 to the measuring-target surface status value calculating unit 12, and the process ends.

On the other hand, when the paper has not been detected in Step S200 and the process proceeds to Step S210, the control section 10c outputs an error signal, and the process proceeds to Step S200.

The printing device 100 notifies a user that a print sheet is not loaded, for example, by turning on a red lamp or the like on the basis of the error signal.

Next, the flow of the process for predicting a measuring-target surface status in Step S106 which is performed by the measuring-target surface status value calculating unit 12 and the prediction unit 13 will be described with reference to FIG. 7.

Figure 7:
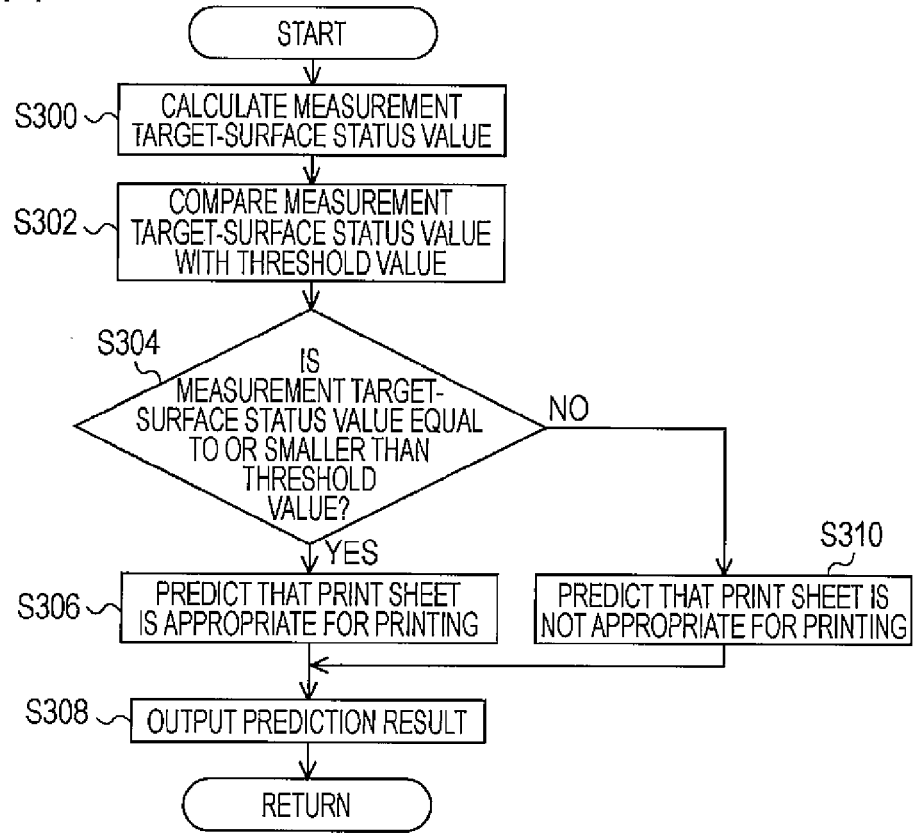
FIG. 7 is a flowchart showing a process for predicting a measuring-target surface status that is performed by a measuring-target surface status value calculating unit 12 and a prediction unit 13 according to an embodiment of the invention.

Here, FIG. 7 is a flowchart showing the process for predicting a measuring-target surface status that is performed by the measuring-target surface status value calculating unit 12 and the prediction unit 13.

In Step S106, when the process for predicting a measuring-target surface status is performed, as shown in FIG. 7, first, the process proceeds to Step S300, and the measuring-target surface status value calculating unit 12 calculates a measuring-target surface status value representing the status of the measuring-target surface based on the image data input in Step S104, and the process proceeds to Step S302.

In Step S302, the prediction unit 13 compares the measuring-target surface status value (the RMS granularity or the total amount of power) calculated in Step S300 with a threshold value Th1 or Th2 set in advance for determination, and the process proceeds to Step S304.

In Step S304, the prediction unit 13 determines whether the measuring-target surface status value is equal to or smaller than the threshold value based on the result of comparison in Step S302. When the measuring-target surface status value is determined to be equal to or smaller than the threshold value (Yes), the process proceeds to Step S306. On the other hand, when the measuring-target surface status value is determined to be larger than the threshold value (No), the process proceeds to Step S310.

When the process proceeds to Step S306, the prediction unit 13 predicts (determines) that the status of the measuring-target surface is appropriate for printing, and thus the process proceeds to Step S308.

In Step S308, the prediction unit 13 outputs the prediction result acquired in Step S306 or in Step S310 to the sorting unit 14, and the process ends.

In addition, when the process proceeds to Step S310, the prediction unit 13 predicts (determines) that the status of the measuring-target surface is not appropriate for printing, and the process proceeds to Step S308.

Next, the operation according to this embodiment will be described with reference to FIGS. 8A, 8B, 9A and 9B.

Figure 8B:
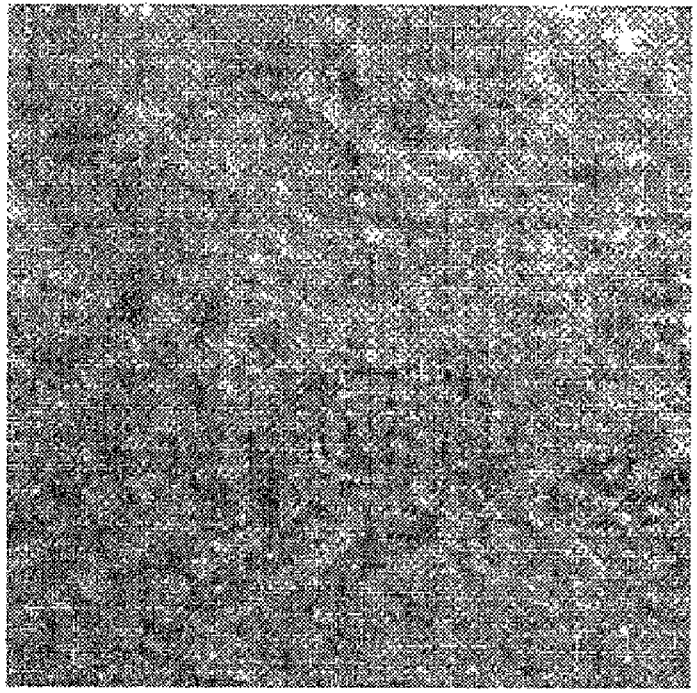
FIG. 8B is a diagram showing an example of an image of a measuring-target surface having a status inappropriate for printing.
Figure 8A:
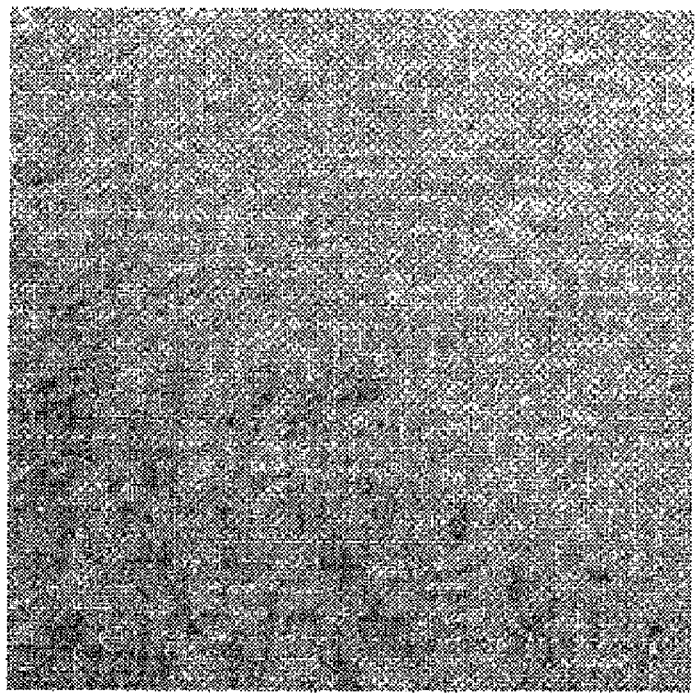
FIG. 8A is a diagram showing an example of an image of a measuring-target surface having a status appropriate for printing.
Figure 9B:
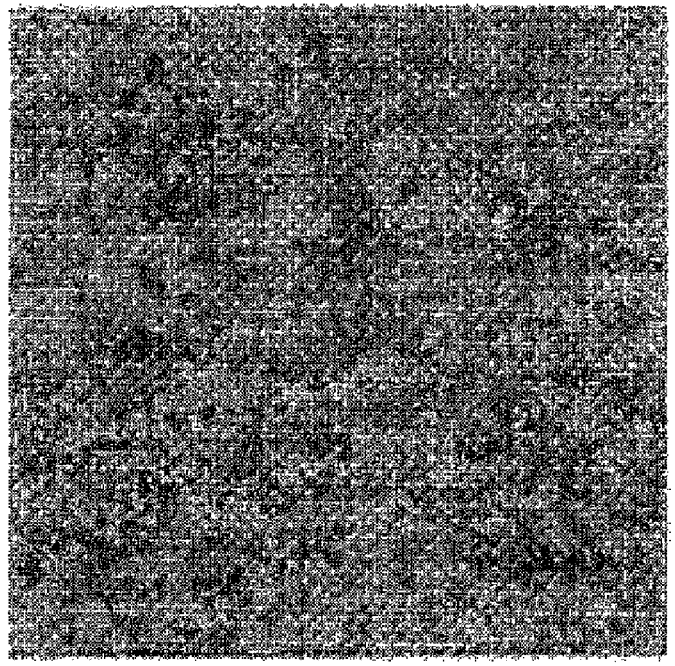
FIG. 9B is a diagram showing an example of the result of printing on a print sheet that has been predicted to be inappropriate for printing.
Figure 9A:
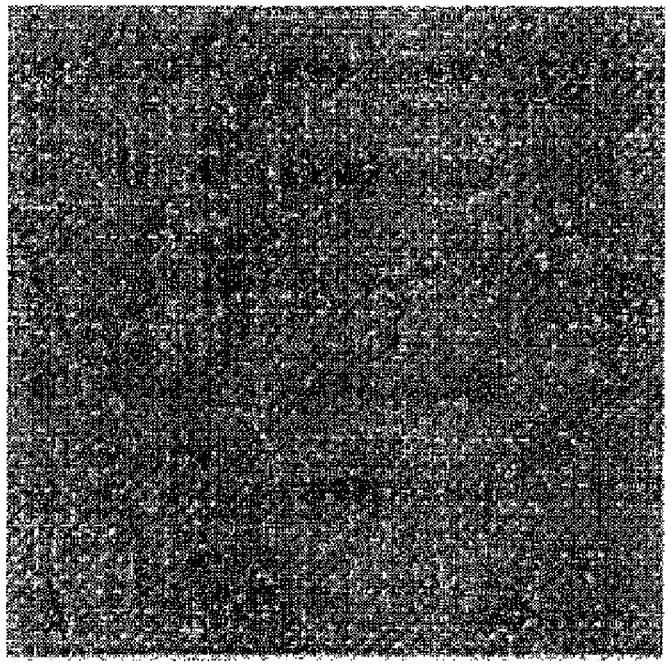
FIG. 9A is a diagram showing an example of the result of printing on a print sheet that has been predicted to be appropriate for printing.

Here, FIG. 8A is a diagram showing an example of an image of a measuring-target surface having a status appropriate for printing. FIG. 8B is a diagram showing an example of an image of a measuring-target surface having a status inappropriate for printing. In addition, FIG. 9A is a diagram showing an example of the result of printing on a print sheet that has been predicted to be appropriate for printing. FIG. 9B is a diagram showing an example of the result of printing on a print sheet that has been predicted to be inappropriate for printing.

When a sorting direction is input (branching for "Yes" in Step S100) to the printing device 100 from an external sorting direction terminal, the measuring-target surface image data generating unit 10 performs a process for generating measuring-target surface image data (Step S102).

When the process for generating measuring-target surface image data is performed, the measuring-target surface image data generating unit 10 determines whether a print sheet is loaded in the print sheet loading unit 11 based on the sensor signal transmitted from the print sheet loading unit 11 by using the control section 10c (Step S200).

Here, the sensor for detecting a print sheet is assumed to be configured by a separation-type photo sensor employing an infrared light emitting diode on the light emitting side and a high-sensitivity photo transistor on the light receiving side. When a print sheet is loaded, the light emitting side is configured to block light to the light receiving side. On the other hand, when a print sheet is not loaded, the light receiving side is configured to receive light from the light emitting side. In other words, a print sheet is detected by blocking light of the light emitting diode by using the print sheet loaded in the print sheet loading unit 11.

In particular, when a print sheet is loaded in the print sheet loading unit 11, light cannot reach the light receiving unit, and accordingly, the sensor signal (a signal indicating that a print sheet is loaded) at that moment is output to the control section 10c. The control section 10c determines that a print sheet is detected based on the sensor signal (branching for "Yes" in Step S200).

When the print sheet is detected, the control section 10c outputs a direction for inputting light fluxes transmitted from the light source to the measuring-target surface of the print sheet to the light input section 10a (Step S202) and outputs an image pickup direction to the image pickup section 10b (Step S204).

The light input section 10a drives the light source (an LED or the like) so as to emit light in accordance with the direction for input from the control section 10c and emits the light fluxes transmitted from the light source through the light collecting lens onto the measuring-target surface of the print sheet loaded in the print sheet loading unit 11. Here, the print sheet loading unit 11 is configured such that a plurality of print sheets can be stacked to be loaded therein, and the light fluxes are incident to a print sheet loaded uppermost.

The image pickup section 10b receives reflection fluxes of the incident light fluxes which are reflected from the measuring-target surface within a predetermined reflection angle by using sensor cells through the light collecting lens, based on the image pickup direction transmitted from the control section 10c and performs a photoelectric conversion process for the received reflection light fluxes so as to generate pixel signal data. Then, the generated pixel signal data is converted into digital pixel data by an A/D converting unit so as to be output to the control section 10c. The reflection light fluxes are received by the sensor cells for a predetermined exposure time by using an electronic shutter function and ALC.

When acquiring the digital pixel data from the image pickup section 10b (Step S206), the control section 10c outputs image data of the measuring-target surface which is constituted by the pixel data to the measuring-target surface status value calculating unit 12 (Step S208).

When a print sheet is not loaded in the print sheet loading unit 11 and a print sheet is not detected (branching for "No" in Step S200), the control section 10c turns on a light emitting element (red LED or the like) which is not shown in the figure by outputting an error signal to a lighting section of the light emitting element and notifies the user that a print sheet is not loaded.

The paper detection process (Step S200), the processes of outputting a light input direction and an image pickup direction (Steps S202 and S204), and the pixel data acquiring process and the image data output process (Steps S206 and S208) in the control section 10c are performed by loading a special purpose program stored in the ROM 64 in the RAM 62 and executing the loaded program by the CPU 60.

When the image data of the measuring-target surface is input from the measuring-target surface image data generating unit 10 to the measuring-target surface status value calculating unit 12 (branching for "Yes" in Step S104), the printing device 100 performs a process of predicting the status of the measuring-target surface based on the input image data by using the measuring-target surface status calculating unit 12 and the prediction unit 13 (Step S106).

When the process of predicting a status of the measuring-target surface is started, the measuring-target surface status value calculating unit 12, first, performs a grey scale process for the image data of the measuring-target surface. Then, the measuring-target surface status value calculating unit 12 calculates RMS granularity $\delta_p$ of the image data of the measuring-target surface for the scaled image data (for example, 8 bits (0 to 255)) by using following Equation (1) as a status value of the measuring-target surface (Step S300). The process of calculating the status value of the measuring-target surface is performed by loading a special program stored in the ROM 64 into the RAM 62 and executing the loaded program by the CPU 60.

Equation (1)

$$\delta_P = \sqrt{\frac{1}{N}\sum_{n=1}^{N}(D_i - D_A)^2} \quad (1)$$

In Equation (1), N denotes the total number of pixels of the image of the measurement-target surface, $D_i$ denotes density distribution (density values of pixels), $D_A$ denotes an average density of the image of the measurement-target surface.

The RMS granularity $\delta_p$, as shown in Equation (1), is a standard deviation of the density distribution $D_i$, and represents better granularity as the value thereof decreases.

Here, as an example, it is assumed that the RMS granularity is calculated as $\delta_p$=14.6.

When the RMS granularity $\delta_p$ is calculated, the prediction unit 13 compares $\delta_p$ with a threshold value th1 that is stored in the ROM 64, the storage device 70, or the like in advance for a determination process (Step S302). Here, it is assumed that th1=15. This threshold value is set based on the type and quality of the print sheet. For example, in a case where the RMS granularity (average) of a gloss-type sheet for a laser printer is 16 and the RMS granularity (average) of a gloss-type sheet for an ink jet printer is 15, the threshold value, for example, set to be 15.

When $\delta_p$ having a value of 14.6 is compared to th1 having a value of 15, $\delta_p$ has a value equal to or smaller than th1 (branching for "Yes" in Step S304), and thus the prediction unit 13 predicts that the status of the measurement-target surface is a status appropriate (normal) for printing (Step S306) and outputs the result of the prediction to the sorting unit 14 (Step S308).

In other words, uniformity of over-exposure due to normal reflection is determined based on the degree of granularity (the magnitude of RMS granularity), and the status of the surface of a paper sheet is predicted based on the result of the determination.

In addition, in the prediction unit 13, the process of comparing the RMS granularity with the threshold value th1 for determination and the prediction process on the basis of the result of the comparison (Steps S302, S304, and S306) and the process of outputting the result of prediction (Step S308) are performed by loading a special program stored in the ROM 64 into the RAM 62 and executing the loaded program by using the CPU 60.

When the result of prediction is input from the prediction unit 13 (branching for "Yes" in Step S108), the input result of the prediction indicates a status appropriate for printing, and accordingly, the sorting unit 14 determines that the print sheet (one sheet positioned uppermost) loaded in the print sheet loading unit 11 is appropriate for printing (branching for "Yes" in Step S110). Accordingly, the sorting unit 14 outputs a transport direction to a transport mechanism included in the sorting unit so as to drive the transport mechanism and transports the print sheet (one sheet positioned uppermost) loaded in the print sheet loading unit 11 to the normal paper tray 15 (Step S112).

The sorting process (Steps S110 and S112) in the sorting unit 14 is performed by loading a special program stored in the ROM 64 into the RAM 62 and executing the loaded program by using the CPU 60 for performing a determination process and a control process for a transport mechanism (not shown).

Next, the operation of the measurement-target surface status value calculating unit 12 in a case where the calculated RMS granularity $\delta_p$ is 17.3 will be described.

In this case, since $\delta_p$ having a value of 17.3 is compared with th1 having a value of 15, $\delta_p$ is determined to have a value larger than th1 (branching for "No" in Step S304).

Accordingly, the prediction unit 13 predicts (determines) that the measurement-target surface is in a status inappropriate (abnormal) for printing (Step S310) and outputs the result of the prediction to the sorting unit 14 (Step S308).

When the result of prediction is input from the prediction unit 13 (branching for "Yes" in Step S108), the input result of the prediction indicates a status inappropriate for printing, and accordingly, the sorting unit 14 determines that the print sheet (one sheet positioned uppermost) loaded in the print sheet loading unit 11 is inappropriate for printing (branching for "No" in Step S110). Accordingly, the sorting unit 14 outputs a transport direction to a transport mechanism included in the sorting unit so as to drive the transport mechanism and transports the print sheet (one sheet positioned uppermost) loaded in the print sheet loading unit 11 to the abnormal paper tray 16 (Step S116).

The above-described series of processes are repeated for print sheets loaded in the print sheet loading unit 11. Then, when checking a status that a print sheet is not detected based on the sensor signal transmitted from the print sheet loading unit 11, the control section 10c determines that the process for all the print sheets is completed (branching for "Yes" in Step S114) and ends the sorting process.

In addition, according to this embodiment, the measurement-target surface status value calculating unit 12 can calculate the total amount of power of spatial frequency components in consideration of human visual characteristics (VTF characteristics) for the image data of the measurement-target surface as the status value of the measurement-target surface.

In particular, the measurement-target surface status value calculating unit 12 transforms the image data of the measurement-target surface into information on spatial frequencies by using a known Fourier transform and corrects (weights) the information on the spatial frequencies by using a parameter of human visual characteristics (VTF) stored in the ROM 64 or the storage device 70 in advance. Then, the measurement-target surface status value calculating unit 12 calculates the total amount of power of the spatial frequencies weighted by the VTF (Step S300). The total amount of the power is calculated by integrating the weighted spatial frequencies.

In the measurement-target surface status value calculating unit 12, the transform process for the information on the spatial frequencies, the correction process by using the VTF, and the process of calculating the total amount of power are performed by loading a special program stored in the ROM 64 into the RAM 62 and executing the loaded program by using the CPU 60. The total amount of the power calculated as above, like the RMS granularity, represents the status (the degree of granularity) of the printing surface and has a value with the human visual characteristics considered. The human visual spatial characteristics for optical information such as a luminosity component or a chromaticity component are acquired based on experiments or the like, and VTF generated in advance based on the experimental results is used as the VTF. Like the RMS granularity, a small value (the total amount of power) represents a small change in the density, and accordingly, the status of the surface of a paper sheet having a small value is determined to be good (non-uniformity of gloss is small). In other words, according to an embodiment of the invention, when the total amount of power weighted by the VTF is small, the degree of granularity having a frequency perceivable to a human is analyzed to be small, and the degree of granularity is apprehended as the non-uniformity of gloss. The smaller the non-uniformity of gloss is, the better (appropriate for printing) the status of the surface of the paper sheet is analyzed to be.

In addition, the prediction unit 13 compares the total amount of the power to a threshold value th2 that is stored in the ROM 64, the storage device 70, or the like in advance for a determination process (Step S302). When the total amount of the power is equal to or smaller than the threshold value th2 (branching for "Yes" in Step S304), the status of the measurement-target surface is predicted (determined) to be appropriate for printing (Step S306). On the other hand, when the total amount of power is larger than the threshold value th2 (branching for "No" in Step S304), the status of the measurement-target surface is predicted to be inappropriate for printing (Step S310).

In the prediction unit 13, the process of comparing the total amount of the power with the threshold value th2 for determination and the prediction process on the basis of the result of the comparison (Steps S302, S304, S306, and S310) are performed by loading a special program stored in the ROM 64 into the RAM 62 and executing the loaded program by using the CPU 60.

Next, in order to clearly show the advantage of the present invention, a difference in the print quality according to a difference in RMS granularity $\delta_p$ will be described.

As described above, an image of a measurement-target surface having RMS granularity $\delta_p$ of 14.6, for example, is as shown in FIG. 8A. On the other hand, an image of a measurement-target surface having RMS granularity $\delta_p$ of 17.3 is as shown in FIG. 8B. FIGS. 8A and 8B are images of completely new measurement-target surfaces on which an image has not been printed.

When both images are compared with each other, it is apparent that the image of the measurement-target surface having RMS granularity $\delta_p$ of 14.6 is smooth (the density change is small) and image of the measurement-target surface having RMS granularity $\delta_p$ of 17.3 is rough (the density change is large).

When an image (a beta image having uniform density) is printed on a print sheet having RMS granularity $\delta_p$ of 14.6, the image is as shown in FIG. 9A. On the other hand, when an image (a beta image having uniform density) is printed on a print sheet having RMS granularity $\delta_p$ of 17.3, the image is as shown in FIG. 9B.

When both images are compared with each other, the image shown in FIG. 9A is smooth (density change is small) and has a good degree of granularity, and the image shown in FIG. 9B has a large density change and a bad degree of granularity. In other words, it can be known that the status of the measurement-target surface is directly reflected on the result of printing.

Thus, as in the printing device 100 according to an embodiment of the invention, a print sheet having a bad measurement-target surface status (predicted to be inappropriate for printing) is transported (sorted) to the abnormal paper tray 16, a print sheet having a good measurement-target surface status (predicted to be appropriate for printing) is transported (sorted) to the normal paper tray 15, and only print sheets sorted into the normal paper tray 15 are used for a printing process, and thereby the printing quality can be stabilized to be in a good status.

As described above, in the printing device 100 according to an embodiment of the invention, the measurement-target surface image data generating unit 10 can generate image data of a measurement-target surface, which is formed mainly by regular reflection light, of a print sheet on which a printing process has not been performed.

In addition, the measurement-target surface status value calculating unit 12 can calculate a status value of the measurement-target surface such as the total amount of power of special frequencies with the RMS granularity and human visual characteristics considered which represents the status relating to appropriateness or inappropriateness of the measurement-target surface for printing.

Accordingly, the status of the printing surface of a print sheet can be represented by a number appropriate for predicting appropriateness for printing. In particular, when the status value of the printing surface is represented by the total amount of power using the VTF characteristics, the human visual characteristics are reflected thereon, and accordingly, for example, in a case where a print sheet determined to be inappropriate for printing based on the RMS granularity generates non-uniformity of density that is not perceivable by human eyes, the print sheet can be determined to be appropriate for printing. Therefore, it is possible to efficiently sort the print sheets.

In addition, the prediction unit 13 can predict whether the status of the measurement-target surface is normal by comparing the RMS granularity or the total amount of power to a threshold value th1 or th2.

In addition, the sorting unit 14 can transport a print sheet having the measurement-target surface in a status appropriate for printing is transported (sorted) to the normal paper tray 15 and transport a print sheet having the measurement-target surface in a status inappropriate for printing is transported (sorted) to the abnormal paper tray 16.

Accordingly, print sheets having measurement-target surfaces predicted to be in a status appropriate for printing and print sheets having measurement-target surfaces predicted to be in a status inappropriate for printing can be appropriately sorted in an automated manner (without using human hands).

In the above-described embodiments, the light input section 10a corresponds to the light input unit described in the first or the fourth aspect or a light input step described in the sixth or tenth aspect, and the image pickup section 10b corresponds to the image pickup unit described in any one of the first, fourth, fifth, and ninth aspects or an image pickup step described in the sixth or tenth aspect. In addition, the measurement-target surface status value calculating unit 12 corresponds to the measurement-target surface status value calculating unit described in any one of the first to third aspects, the prediction unit 13 corresponds to the prediction unit described in the eights aspect, and the sorting unit 14 corresponds to the sorting unit described in the seventh or eighth aspect.

In addition, in the above-described embodiments, Step S300 corresponds to the calculating of the status value of the measurement-target surface described in any one of the fifth, sixth, ninth, and tenth aspects, Steps S302 to S308 correspond to the predicting of whether a defective quality of printing occurs described in any one of the fifth, sixth, ninth, and tenth aspects, and Steps S110 to S114 correspond to the sorting of the print media described in the ninth or tenth aspect.

In addition, in the above-described embodiments, although the configuration of the printing device 100 in which constituent units of the printing device are built in one casing is used, the configuration is not limited thereto. Thus, a configuration in which constituent units of the printing device and the prediction unit 13, the sorting unit 14, the normal paper tray 15, and the abnormal paper tray 16 are divided into separate devices and both devices are interconnected for data communication may be used.

In addition, in the above-described embodiments, although a print sheet has been described as an example of a print medium, however, the print medium is not limited thereto. Therefore, the present invention may be applied to a print medium other than the print sheet.

In addition, in the above-described embodiments, although the RMS granularity and the total amount of power are configured to be calculated as status values of the measurement-target surface, however, the status value is not limited thereto. Therefore, another value representing the status of the measurement-target surface may be configured to be calculated.

In addition, in the above-described embodiments, although the status of one side of the print sheet loaded in the print sheet loading unit 11 is configured to be predicted for sorting, the present invention is not limited thereto. Therefore, a configuration in which statuses of both sides of the print sheet are predicted and the print sheet is sorted based on the prediction result of both sides may be used. For example, in the print sheet loading unit 11, a mechanism for turning a print sheet over may be provided.

In such a case, three statuses including both sides inappropriate for printing, one side appropriate for printing, and both sides appropriate for printing can be predicted, and accordingly, it is possible to prevent a miss operation of printing on a side having a status inappropriate for printing more assuredly by sorting on the basis of the statuses.

In addition, the present invention is not limited to a printing device of an ink jet type, and the present invention can be applied to printers of various types including a laser type, a heat-transfer type, a sublimation type, an impact dot type, and the like.

In addition, in the above-described embodiments, although a configuration in which various special-purpose computer programs stored in the ROM 64 are loaded in the RAM 62 and the loaded programs are executed by the CPU 60 is used, the present invention is not limited thereto. Therefore, a configuration in which programs installed to the storage device 70 though a storage medium such as a CD-ROM, a DVD-ROM, or a flexible disk (FD) or programs installed to the storage device 70 though a communication network such as the Internet are loaded in the RAM 62 and the loaded programs are executed by the CPU 60 may be used.

What is claimed is:

1. A printing device comprising:
   a light input unit that inputs light fluxes emitted from a light source to a measurement-target surface of a print medium on which an image is printed at a predetermined incidence angle;
   an image pickup unit that picks up an image of the measurement-target surface by collecting reflection light fluxes, which are reflected from the measurement-target surface of the print medium within a predetermined range of reflection angles, for the light fluxes input by the light input unit, receiving the collected light fluxes using a plurality of light receiving elements, and performing a photoelectric conversion process for the light fluxes received by the plurality of light receiving elements; and
   a measurement-target surface status value calculating unit that calculates a status value of the measurement-target surface representing a status relating to appropriateness or inappropriateness of the measurement-target surface of the print medium prior to printing based on image data having luminance information of the image picked up by the image pickup unit, wherein
   the measurement-target surface status value calculating unit calculates the status value of the measurement-target surface based on an RMS (Root Mean Square) granularity that is a standard deviation of distribution of the luminance information included in the image data of the measurement-target surface in order to determine a uniformity of gloss on the print medium.

2. The printing device according to claim 1, further comprising:
   a frequency converting unit that converts the luminance information included in the image data of the measurement-target surface into information on spatial frequencies; and
   a correction unit that corrects the information on spatial frequencies converted by the frequency converting unit using a parameter of human visual spatial frequency characteristics (VTF: Visual Transfer Function),
   wherein the measurement-target surface status value calculating unit calculates the status value of the measurement-target surface based on the total amount of power of the spatial frequencies which have been corrected by the correction unit.

3. The printing device according to claim 1, wherein the light input unit and the image pickup unit are disposed such that an incidence angle of a flux positioned in the center or an approximate center of the input light fluxes and a reflection angle of a light flux positioned in the center or an approximate center of the reflection light fluxes received by the plurality of light receiving elements are identical to each other.

4. The printing device according to claim 1, further comprising a sorting unit that sorts print media into types according to the status values of the measurement-target surfaces based on the status values of the measurement-target surfaces calculated by the measurement-target surface status value calculating unit.

5. The printing device according to claim 4, further comprising a prediction unit that predicts whether a defective quality of printing occurs in a case where a print medium corresponding to the status value of the measurement-target surface is used for printing based on the status value of the measurement-target surface which is calculated by the measurement-target surface status value calculating unit, wherein the sorting unit sorts the print medium based on the result of prediction of the prediction unit.

6. The printing device according to claim 1, wherein the status value is calculated based only on image data picked up from the print medium.

7. A non-transitory recording medium having embodied thereon a program that allows a computer to perform calculating a status value of a measurement-target surface representing a status relating to appropriateness or inappropriateness of the measurement-target surface of a print medium prior to printing based on image data including luminance information of an image acquired by an image pickup unit that picks up the image of the measurement-target surface by collecting reflection light fluxes, which are reflected from the measurement-target surface of the print medium within a predetermined range of reflection angles, for light fluxes incident at a predetermined incidence angle to the measurement-target surface of the print medium, receiving the collected light fluxes using a plurality of light receiving elements, and performing a photoelectric conversion process for the light fluxes received by the plurality of light receiving elements, wherein the status value of the measurement-target surface is calculated based on an RMS (root mean square) granularity that is a standard deviation of distribution of the luminance information included in the image data of the measurement-target surface in order to determine a uniformity of gloss on the print medium.

8. A recording medium according to claim 7, wherein the program further allows a computer to perform sorting print media into types according to the status values of the measurement-target surfaces based on the status values of the measurement-target surfaces calculated by the calculating of a status value.

9. The recording medium according to claim 7, wherein the status value is calculated based only on image data picked up from the print medium.

10. A method of controlling a printing device, the method comprising:

inputting light fluxes emitted from a light source to a measurement-target surface of a print medium at a predetermined incidence angle;

picking up an image of the measurement-target surface by collecting reflection light fluxes, which are reflected from the measurement-target surface of the print medium within a predetermined range of reflection angles, for the light fluxes input by the inputting of light fluxes, receiving the collected light fluxes using a plurality of light receiving elements, and performing a photoelectric conversion process for the light fluxes received by the plurality of light receiving elements; and calculating a status value of the measurement-target surface representing a status relating to appropriateness or inappropriateness of the measurement-target surface of the print medium prior to printing based on image data having luminance information of the image picked up by the picking up of an image, wherein the status value of the measurement-target surface is calculated based on an RMS (root mean square) granularity that is a standard deviation of distribution of the luminance information included in the image data of the measurement-target surface in order to determine a uniformity of gloss on the print medium.

11. The method according to claim 10, further comprising sorting print media into types according to the status values of the measurement-target surfaces based on the status values of the measurement-target surfaces calculated by the calculating of a status value.

12. The method according to claim 10, wherein the status value is calculated based only on image data picked up from the print medium.

* * * * *